United States Patent [19]

Macy

[11] Patent Number: 4,716,030

[45] Date of Patent: Dec. 29, 1987

[54] METHOD FOR DETECTION OF EXOGENOUS OR ACTH STIMULATED GLUCOCORTICOIDS IN DOMESTIC ANIMALS

[75] Inventor: Dennis W. Macy, Ft. Collins, Colo.

[73] Assignee: Colorado State University Research Foundation, Ft. Collins, Colo.

[21] Appl. No.: 727,288

[22] Filed: Apr. 25, 1985

[51] Int. Cl.[4] ............................................. A61K 49/00
[52] U.S. Cl. ........................................................ 424/9
[58] Field of Search ........................................... 424/9

[56] References Cited

PUBLICATIONS

Chem. Abst. Gen. Subj. Index-vol. 86-95, (1977-1981) p. 2743GS.
Johnson, R. K.: Insulinoma in the Dog, Vet Clin. North Am., 7(3): 629-635.
Behrans, O. K. and Broner, W: Glucagon, Vitamins and Hormones, vol. XVI-16: 263-301, Academic Press, New York (1958).
Kemppainen, R. J., et al., Adrenocortical Suppression in the Dog Given a Single Intramuscular Dose of Prednisone or Triamcinoline Acetonide, Am. J Vet Res., vol. 42, No. 5, 204-206.
Wellman, M. L., et al., Immunoassay for the Steroid-Induced Isoenzyme of Alkaline Phosphatase in the Dog, Am. J Vet Res., vol. 43, 1200-1204.
Adrenocortical Suppression in the Dog After a Single Dose of Methylprednisolone Acetate, Kemppainen, R. J., et al., Am. J Vet Res., vol. 42, No. 5, 822-824.
Sequential Morphologic and Clinicopatholic Alterations in Dogs with Experimentally Induced Glucocorticoid Hepatopathy, Badylak, S. F., et al., Am. J Vet Res., vol. 42, No. 5, 1310-1317.

*Primary Examiner*—Sam Rosen
*Attorney, Agent, or Firm*—Dorr, Carson, Sloan & Peterson

[57] ABSTRACT

A method for the detection of exogenously administered, or ACTH stimulated, glucocorticoids in domestic animals is provided by first injecting glucagon into a suspected glucocorticoid abused animal and then monitoring the animal's blood glucose levels against an appropriate control over a two hour period. The test measures hepatic carbohydrate metabolism; consequently it is capable of detecting glucocorticoid abuse regardless of the chemical nature of the carrier or base in which the glucocorticoid or ACTH was delivered.

9 Claims, 4 Drawing Figures

METHOD FOR DETECTION OF EXOGENOUS OR ACTH STIMULATED GLUCOCORTICOIDS IN DOMESTIC ANIMALS

BACKGROUND OF THE INVENTION

1. Field of the Invention

This invention relates generally to methods for detecting abusive use or stimulation of glucocorticoids in domestic animals, particularly in the context of the medical/legal issues associated with the performance of certain animals, e.g., race horses, racing greyhounds, sled dogs, etc., used in sporting contests. More specifically, this invention relates to methods for detecting use of supraphysiological levels of glucocorticoids by chemical analysis directed at alteration in animal liver glycogen metabolism function. Central to any chemical analysis is an understanding of the terms glycogen, glycogenesis, glycogenolysis and glucocorticoids.

Glycogen

Glycogen is the chief storage form of carbohydrate in animals and is analogous to starch in plants. The principle organ in which glycogen is stored in the body is the liver. The process of glycogen synthesis (glycogenesis), and that of its breakdown (glycogenolysis) is known to proceed by two separate pathways.

Glycogenesis

The initial reaction required for the entrance of glucose into the series of metabolic reactions which culminate in the synthesis of glycogen is phosphorylation of glucose at the C-6 position. Glucose is phosphorylated by adenosine triphosphate (ATP) in the liver by an irreversible enzymatic reaction which is catalyzed by a specific glucokinase. This undirectional phosphorylation permits the accumulation of glucose in the liver cell since the phosphorylated sugars do not pass freely in and out of the cell in contrast to the readily diffusable free sugars. The trapped glucose-6-phosphatase is converted to glucose-1-phosphatase, a reaction catalyzed by phosphoglucomutase. Glycogen is synthesized from the glucose-1-phosphate through reactions involving the formation of uridine derivatives. In the presence of polysaccharide primers and the enzyme glycogen synthetase, the glucose moiety of the urine derivatives is linked to the polysaccharide. Through repeated transfers of glucose, the polysaccharide chain is eventually lengthened until a glycogen molecule is formed.

Glycogenolysis

The breakdown of liver glycogen to glucose takes place by a second pathway. In the presence of inorganic phosphate, the glucose linkage of glycogen is successfully broken by active phosphorylases. Epinephrine and glucagon influence the phosphorolytic breakdown of glycogen to glucose. The phosphorolytic enzyme exists in the liver in two forms: an active form designated liver phosphorylase (LP) which contains phosphate and an inactive form designated dephosphorylase (dephospho-P), in which phosphate has been removed. The transformation between the active and the inactive forms are catalyzed by specific kinase enzymes. Normally the level of LP is low and the epinephrine and glucagon shifts the equilibrium toward a higher level of LP. The net result is an increased phosphorolytic breakdown of glycogen to glucose. A hyperglycemia is observed clinically following the injection of either of these two hormones.

Glucocorticoids

Glucocorticoids promote liver glycogen storage. This increase in liver glycogen storage has been attributed to glucocorticoid enhancement of gluconeogenesis, hyperglycemia, decreased glycogenolysis and decreased glucose oxidation.

Glucagon

Glucagon has been used in certain diagnostic procedures as well as in various pharmaceutical treatments. It is a polypeptide secreted by the alpha cells on the pancreas. The primary structure of porcine, bovine and human glucagon are identical. Glucagon is produced as a by-product of insulin production from pork and beef pancreases. Injections of glucagon are known to elevate blood glucose levels by causing hepatic glycogenolysis. Furthermore, it is known that under standardized conditions, glucagon induces reproducable hyperglycemia in test animals.

However, despite the knowledge of glycogenesis and glycogenolysis, it has not been heretofore fully appreciated that the intravenous administration of glucagon (glucagon tolerance test) may be used to detect the excessive storage of liver glycogen associated with supraphysiologic levels of glucocorticoids.

2. Prior Art

Injection tests have been used in the dog to differentiate pancreatic tumorbearing dogs in which insulin release is stimulated by the transient hyperglycemia product following glucagon administration; blood glucagon levels are then measured. (See Johnson RK: Insulinoma in the dog. Vet Clin North Am 7(3):629–635, 1977). The cat has also been used as an in vivo means of assaying small quantities of glucagon. (See Behrens OK, Broner W.: Glucagon, Vitamin, and Hormone, vol XVI-16:263–301, Academic Press, New York 1958.

Moreover, when used properly, glucocorticoids can be beneficial in alleviating inflammation before excessive tissue damage occurs. However, glucocorticoids do have the potential to be abused. Numerous reports document rapid suppression of the Hypothalamic-Hypophysis-Adrenocortical (HHA) axis after parenteral corticosteroid use. Along with injection, oral administration topical therapy has also been incriminated in suppression of and hypothalamic release of corticotropin-releasing factor and hypophysis ACTH, thus producing secondary adrenal atrophy. In addition to the detrimental effects of glucocorticoids on the HHA axis, they are also associated with a wide variety of detrimental effects such as delayed wound healing, infection, protein catabolism, steroid arthropathies and other Cushingoid conditions. The ability of exogenous glucocorticoids (or endogenous glucocorticoids produced by nonphysiological ACTH stimulation) to mask pain associated with inflammation is also well known. Intravenous and intramuscular injections of these substances, as well as their direct injection into the joints of race animals, are illegal, but are not uncommon practices. Consequently, the need for a simple and accurate test to detect evidence of such abuses clearly exists. This need is presently being met by various hematologic (neutrophilia, neutropenia, eosinopenia), hormonal (depressed ACTH response) and biochemical (serum, alkaline, phosphatase increases) tests which are, to varying degrees, capable of qualitative detection of glucocorticoid administration. However, none of these tests are sufficiently pronounced or consistent enough to be regarded as reliable indicators of exogenous administration of glucocorticoids and/or nonphysiologic ACTH stimulation of elevated glucocorticoid levels. Moreover, they are not well suited to field use. Liver biopsy for detection of steroid hepatopathy is a sensitive and consistent test; but it is generally regarded as being too risky and impractical in most performance animal test situations. Consequently, the most widespread method currently used for detecting use of exogenous glucocorticoids and ACTH stimulation depends upon detection of the propylene glycol base often used in many glucocorticoid or ACTH formulations. However, this technique is totally ineffective in detecting aqueous preparations of those glucocorticoids which are frequently injected into the joints of race animals. Hence complete definitions of the role of glucocorticoids in race animal sporting events has been hampered by the lack of a specific and sensitive assay for glucocorticoids. Without a satisfactory technique to determine the presence of glucocorticoids in readily available biologic substances such as the animal's blood, any accusations or conclusions regarding the possible abuse of glucocorticoids must remain presumptive or tentative. In order to obviate this problem, Applicant has developed a safe, reliable test for detecting evidence of supraphysiologic glucocorticoid levels, regardless of the chemical nature of the base or carrier in which the glucocorticoid is administered. This test also has other diagnostic aspects which are covered in, Roberts, Stevens M., et al, Effect of Opthalmic Prednisolone Acetate on the Canine Adrenal Gland and Hepatic Function, Am. J. Vet. Res., Vol. 45, No. 9 (September 1984) which is specifically incorporated herein by reference.

SUMMARY OF THE INVENTION

My method for the detection of exogenous glucocorticoids, or the use of ACTH to stimulate endogenous glucocorticoids, follows from the fact that pharmacological doses of glucocorticoids act to increase hepatic glycogen storage and gluconeogenesis while decreasing glucose uptake in peripheral tissues. Such glycogen deposition is increased in both fasted and fed animals. The increased glycogen deposition is believed to be the result of corticosteroid induced glycogen synthetase activity due to blockage of the inhibitory affect of glycogen phosphorylase "A" on glycogen synthetase. This enzyme converts glycogen synthetase from the inactive "A" form to the active "B" form. Glycogen breakdown may also be inhibited as a result phosphorylase "A" inactivation. In any case, glucagon stimulates the formation of cyclic AMP from ATP in the liver and leads to activation of phosphorylase, the rate-limiting enzyme in the conversion of glycogen to glucose. Although other changes may also occur, the glucagon induced rise in blood glucose concentration upon which this test is based is believed to be principally a result of glycogenolysis. The test is therefore an indirect measure of hepatic glycogen accumulation normally associated with supraphysiological levels of glucocorticoids. The test involves measuring blood glucose levels at various times, e.g., 0, 5, 15, 30, 60 and 120 minutes, over about a two hour period following intravenous injection of glucagon. The time period around the 30 minute blood glucose level post glucagon administration can be a particularly important period in this test methodology since the greatest differentials between normal blood glucagon levels and the elevated levels resulting from glucagon abuse tend to occur around this point in time (See FIG. 1). Our test is technically simple, economically inexpensive and, as indicated by later portions of this patent application, extremely sensitive. For example, the use of topical glucocorticoids in the eyes of dogs was readily detected by the test. Again the test also can detect supraphysiological levels of glucocorticoids produced by ACTH stimulation. Moreover, because the test indirectly measures hepatic carbohydrate metabolism, it is effective in detecting glucocorticoid use regardless of the carrier or base in which an abused glucocorticoid or ACTH is delivered. Consequently, glucocorticoids administered in aqueous carriers will be detected just as readily as those administered in propylene glycol carriers. The test may be used as a preliminary screening test in the field, or it may be used in conjunction with other tests carried out in laboratories (e.g., liver biopsy). More preferably, however, the test can be used as an independent, conclusive test in its own right in field test situations. Diagnostic procedures, as well as kits containing premeasured glucagon doses (i.e., for greyhounds, race horses etc.) to carry them out, can be readily prepared based upon the disclosures made herein.

For example, animals in which glucocorticoid administration is suspected could be administered a premeasured dose of glucagon. Blood can then be collected at one or more select points in time, e.g., at 15, 30 and 60 minutes after injection in fluoride-containing tubes (to stop glycolysis) and an analysis using reagent strips for testing glucose levels in whole blood can then be performed immediately as a conclusive test. In the alternative, because reagent strips are sometimes not as sensitive as photometric methods for analysis of glucose, samples in which blood glucose levels are not clearly within the normal or abusive ranges could then be subjected to a more accurate analytical determination at a later time without fear of compromising the accuracy of the test.

DESCRIPTION OF THE DRAWINGS

For a fuller understanding of this invention, reference is made to the following description taken in connection with the accompanying drawings, in which.

DESCRIPTION OF THE PREFERRED EMBODIMENTS

The following animal subjects, procedures and exemplary tests are presented as illustrations of my method of detecting glucocorticoid and/or ACTH abuse; these tests illustrate the concepts of this invention, but should in no way be regarded as limitations upon those concepts.

TESTS

Prednisolone acetate

Figure 3:
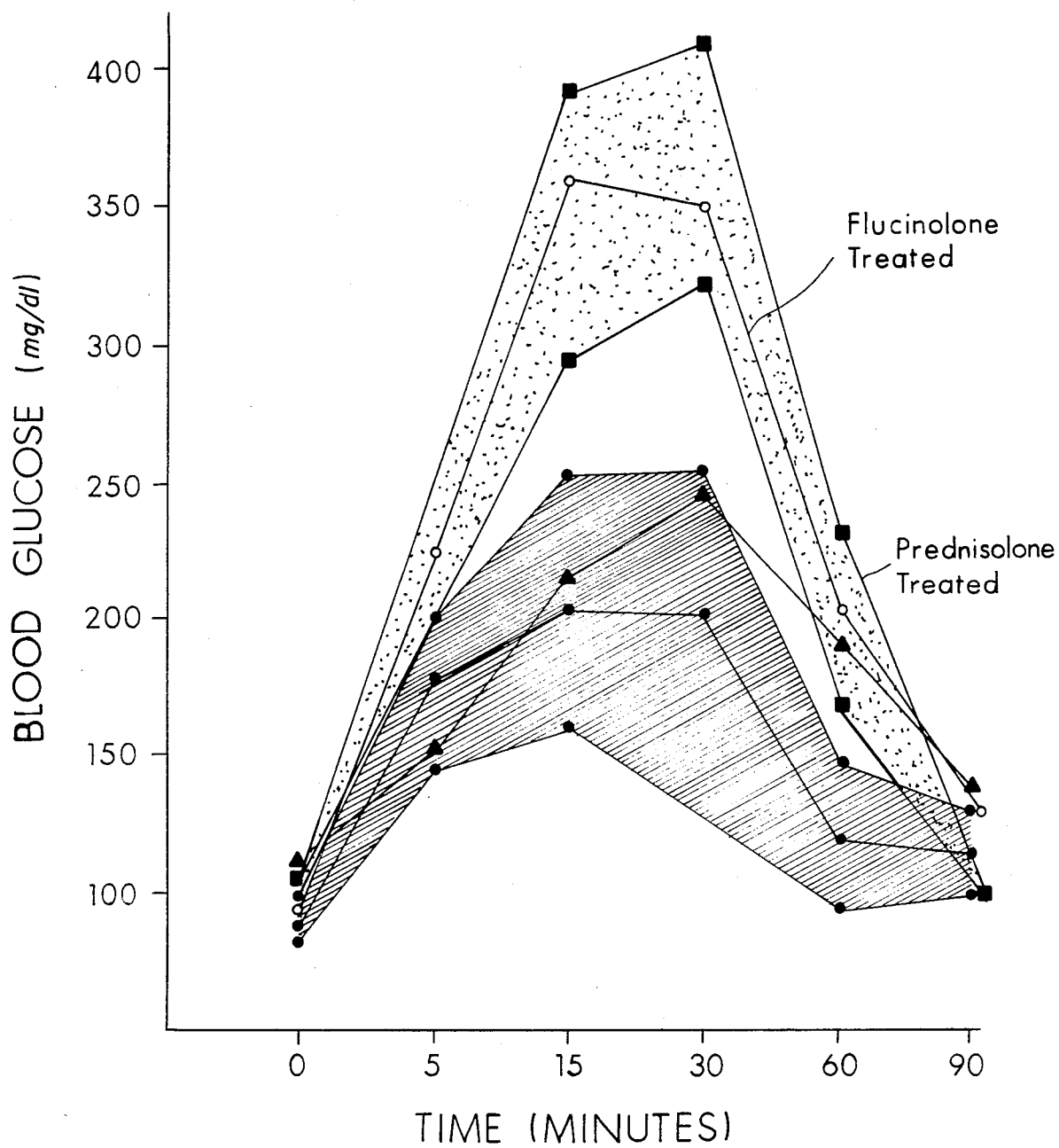
FIG. 3 depicts blood glucose concentrations versus time (in minutes) for normal dogs and horses shown in relation to blood glucose levels when supraphysiological amounts of glucocorticoids such as prednisolone and flucinolone were previously administered.

Five mature, mixed-breed dogs weighing 3.5 to 7 Kg were used to establish the reference curve of glucagon tolerance for normal dogs, i.e., the Pre Treatment high, low and mean curves of FIGS. 1 and 3, and as test subjects in the experiments hereinafter described which resulted in the 2 weeks Treatment (0.75 mg/kg), 4 weeks Treatment (0.5 mg/kg), and Post Treatment Curves of FIG. 3. All of the dogs used were vaccinated against canine distemper, adenovirus type II, parainfluenza, parvovirus (Vanguard), and rabies (Rabguard); dewormed; and quarantined for 4 to 6 weeks. The dogs were dry fed dog food once daily in the morning. The initial evaluation consisted of a general physical and ophthalmic examination. As part of the laboratory tests these dogs received complete blood cell counts, (CBC) serum chemical profile, ACTH stimulation test and glucagon tolerance tests. The dogs were fasted for 24 hours before blood sampling.

Flucinolone

Flucinolone was administered topically as a part of an ear preparation to both external ear canals of a 10 kg normal dog for a period of 21 days in the effective dose of 0.003 mg/kg/day. After the treatment period, a complete serum chemistry panel and CBC profiles were performed in addition to the glucagon tolerance test (0.03 mg/kg IV). Blood glucose levels (mg/dl) following the administration of glucagon were at 0, 119, 5 minutes 232, at 15 minutes 356, at 30 minutes 348, at 60 minutes 241, at 90 minutes 149.

Glucagon Treatment Reference Curves

Glucagon treatment reference curves for normal dogs were determined using a wide range of pharmacologic doses of glucagon in dogs in various age groups: the doses being 0.14 mg/kg (5 adult dogs) and 0.03 mg/kg (11 adult dogs) and (3 juvenile dogs). A reference curve was established for a horse using a dose of 0.03 mg/4.5 kg or 0.00074 mg/kg. All animals were fasted for 24 hours prior to establishing their respective reference curve and were considered normal by all available clinical and biochemical means. Significant to the normal curve is the peak of blood glucose values at 15 minutes. This is in contrast to animals who are under the influence of supraphysiologic levels of glucocorticoids whose peak blood glucose values are at 30 minutes. Note also that despite the wide range of glucagon used in the reference group, peak levels of glucose following IV injections are similar for both test groups of dogs and are markedly similar for the horse.

DETAILS OF AN ILLUSTRATIVE GLUCOCORTICOID TREATMENT DETECTED BY THE METHODS OF THIS INVENTION

A common glucocorticoid, topical prednisolone acetate (1%), was installed into each eye of the dogs tested, four times per day by delivery of 0.05 ml at each treatment from a standard eyedropper bottle dispensing 20 drops/ml. This supplied 4 mg of prednisolone/dog/day or an average of 0.75 mg/kg of body weight/day. The eyes were treated at 0800, 1200, 1700, and 2200 hours daily for 2 weeks. Blood samples were collected after treatment week 2. Treatment was continued at the previous frequency and times for 2 more weeks, using an eyedropper delivering 30 drops/ml. This supplied 2.67 mg of prednisolone/dog/day or an average of 0.5 mg/kg day. Blood samples were collected after treatment week 4. After 4 weeks of topical therapy, all medication was withdrawn, and blood samples were collected 2 weeks after treatment was discontinued. During the treatment period, no effort was made to prevent blinking after instillation of the eyedrops.

OPHTHALMIC EXAMINATION

Complete ophthalmic examinations were performed at weekly intervals. Examination consisted of anterior segment evaluation, using biomicroscopy (Kowa SL-2) and posterior segment evaluation after mydriasis with biomicroscopy and indirect ophthalmoscopy, (Duralite MK1) using a 20 diopter hand lens.

LABORATORY EXAMINATION

Blood samples were collected with an 18-gauge jugular catheter. All samples were collected between 0830 and 1205 hours. Collection times were standardized such that each sample for a particular dog was collected at the same time. Those samples requiring serum were allowed to stand for 15 minutes and were centrifuged, and the serum was separated. Serum chemical profiles and blood glucose determinations were performed on an automated chemistry analyzer (Rotochem IIa, Travenol Laboratories, Inc., Instrument Division, Savage, Md.) at 1230 hours. Serum for cortisol determinations were frozen until all samples could be analyzed as 1 batch. The CBC were performed with the aid of a Coulter counter.

CORTISOL AND GLUCOSE TESTS

Serum glucose values (see FIG. 3) during the glucagon tolerance test (0.14 mg/kg, IV) were determined at 0, 3, 5, 15, 30, 60, and 120 minutes after glucagon administration by use of an automated chemistry analyser (Rotochem II, Travenol Laboratories, Inc., Instruments Division, Savage, Md.). Statistical analysis was completed on a data processing computer system (Eclipse M/600, Data General Corp., West Borough, Mass.) using paired t tests.

Figure 4:
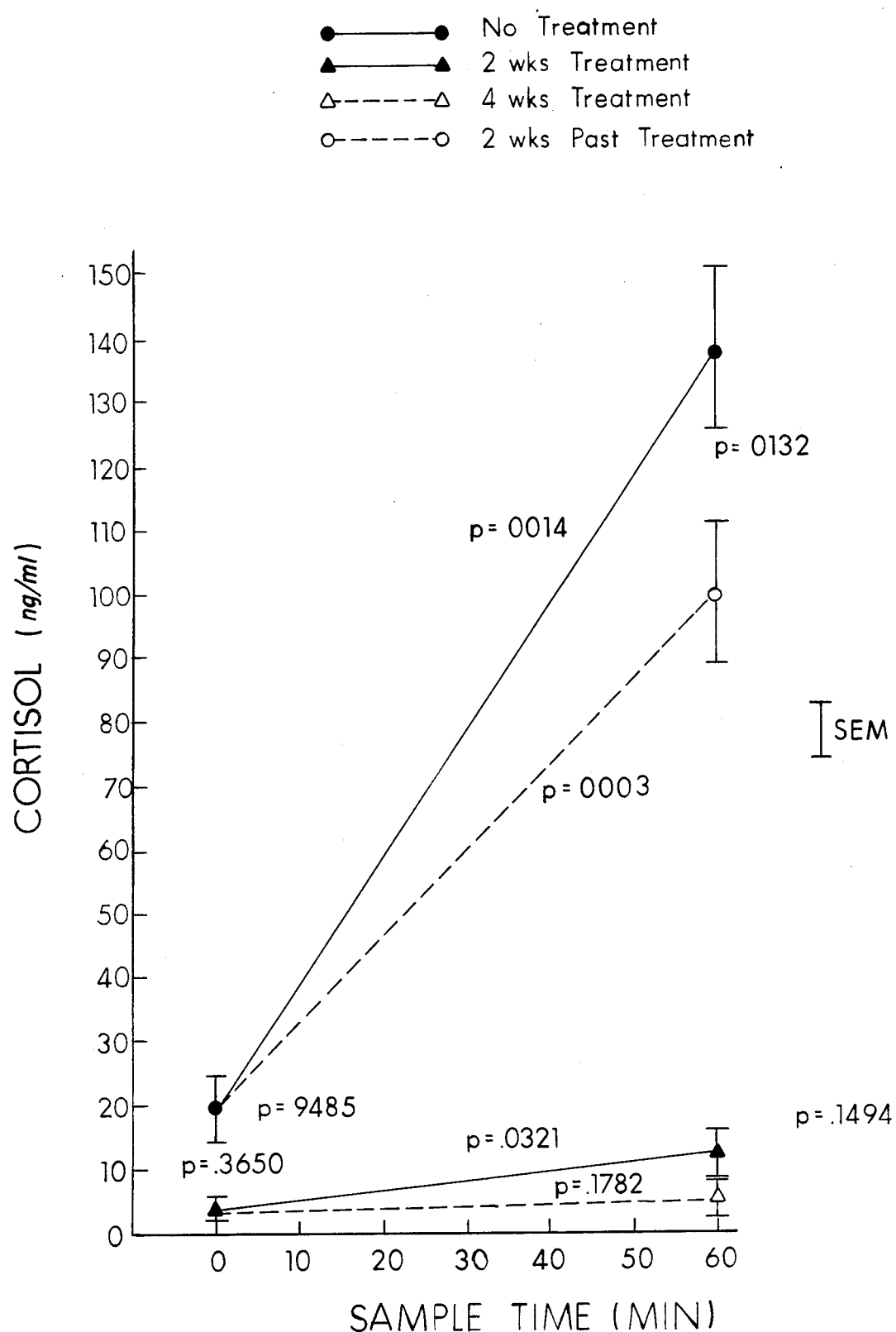
FIG. 4 depicts pre- and post-ACTH mean cortisol values versus time.

Cortisol was quantified (see FIG. 4) by validated radioimmunoassay of serum samples collected immediately before and 60 minutes after ACTH injection (0.55 IU/kg, IV). Sensitivity was $1.98 \pm 10.3$ pg/tube of cortisol. No significant differences existed between pre-ACTH values before and 2 weeks after treatment or during the 2 and 4 week treatment periods pre- and post-ACTH values. Post-ACTH mean values did not return to base-line values 2 weeks after treatment.

RESULTS

All dogs remained healthy and ophthalmic sequels were not detected as a result of topical corticosteroid therapy. Serum chemical and CBC values were altered as follows: The average neutrophil, lymphocyte, and eosinophil absolute counts decreased 24%, 21%, and 74%, respectively. The average monocyte count increased 11%. Overall, the total WBC decreased 22%; however, absolute values never decreased below the normal range used at Colorado State University. Of the 5 dogs tested, 1 developed a progressive increase in serum alkaline phosphatase and alanine aminotransferase values. Peak values after 4 week of topical therapy were 287 IU/L (normal 52 IU/L) and 169 IU/L (normal 27 IU/L), respectively.

Marked suppression of the hypothalamic-hypophysis-adrenocortical (HHA) axis occurred. Resting and post ACTH cortisol values decreased from base-line values of $17.66 \pm 4.10$ ng/ml (X±SEM) and $139.16 \pm 15.74$ ng/ml (X±SEM), respectively, to $3.22 \pm 1.53$ ng/ml (X±SEM) and $13.58 \pm 5.32$ ng/ml (X±SEM), respectively, after 2 weeks of therapy. After 4 weeks of topical therapy, the resting and post ACTH cortisol values decreased to 1.76±0.72 ng/ml (X±SEM) and 4.82±2.57 ng/ml (X±SEM), respectively.

Figure 1:
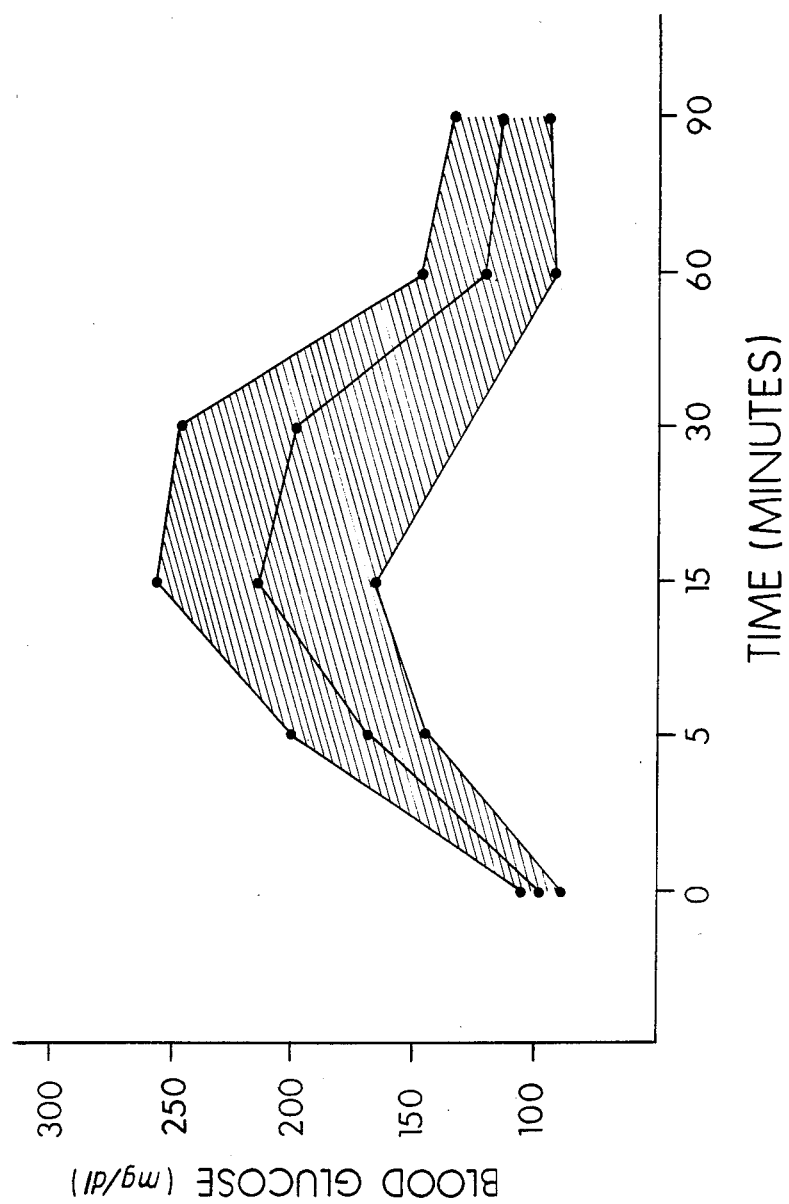
FIG. 1 depicts blood glucose concentrations versus time (in minutes) for normal adult dogs after glucagon injection.
Figure 2:
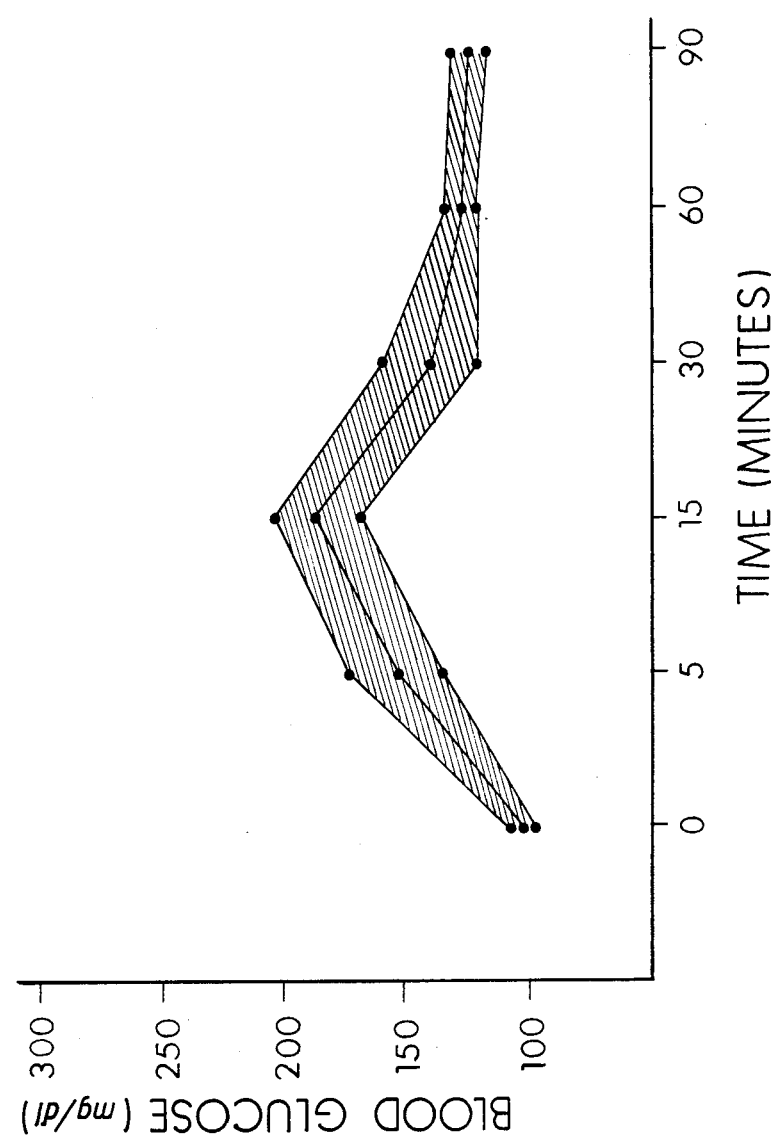
FIG. 2 depicts blood glucose concentrations versus time (in minutes) for normal juvenile dogs after glucagon injection.

There were no significant differences between resting and poststimulation values for the 2 or 4 week treatment periods (P=0.365 and P=0.149, respectively, FIG. 1). These data were pooled for further comparison. The resulting mean serum cortisol values during treatment were 2.49±0.96 ng/ml (X±SEM) resting and 9.20±3.37 ng/ml (X±SEM) after ACTH administration.

The HHA axis did have an improved response to ACTH stimulation after discontinuing therapy for 2 weeks. Significant differences did not exist between resting cortisol values of the base-line and post-treatment samples (P=0.9485, FIG. 1). Post ACTH values remained significantly less for the posttreatment samples compared with the baseline samples (P=0/0132, FIG. 1). Pooled mean cortisol values during treatment were significantly less than those before treatment for resting and post-ACTH values (P=0.0188 and P=0.0003, respectively). Although the treatment group did have some response of the adrenal axis to ACTH stimulation it was less than that seen in the base-line group.

Significant effects were noticed on carbohydrate metabolism as a result of the topical corticosteroid. There were no significant differences between blood glucose values after glucagon stimulation tests for the base-line and posttreatment data. The blood glucose values after 4 weeks of topical therapy were consistently lower than those after 2 weeks of therapy, although the differences were not significant. This may be due to the lower daily dose applied to the eye during the second 2-week period. Significant increases in blood glucose values occurred as a result of topical corticosteroid at 3, 5, 15, 30, and 60 minutes after glucagon administration (P=0.0367, P=0.0302, P=0.0337, P=0.0022, and P=0.0310, respectively). The greatest difference between treatment and no treatment blood glucose values occurred at 30 minutes after glucagon administration (P=0.0022). The mean 30 minute postglucagon stimulation blood glucose after 4 weeks of therapy was 337±19.38 mg/dl (X±SEM), whereas the base-line value was 224.60±7.89 mg/dl (X±SEM). This represents a mean blood glucose mobilization increase of 112.40 mg/dl±19.32 (±SEM).

Glucagon tolerance tests were used to evaluate the effect of topically applied corticosteroids in hepatic carbohydrate metabolism. Therapy produced an exaggerated blood glucose increase on glucagon administration, indicating enhanced hepatic glycogen accumulation and/or mobilization efficiency. The exaggerated blood glucose increase is particularly emphasized by the upper, lightly shaded areas of FIG. 3.

The significant increase in blood glucose during these glucagon tolerance tests demonstrates that glucocorticoids act to increase hepatic glycogen storage and gluconeogenesis and to decrease glucose uptake and use in peripheral tissues. Gycogen deposition is known to be increased in both fasted and fed animals. Increased hepatic glycogen has been previously demonstrated histologically in the dog after glucocorticoid administration. This is most probably a result of corticosteroid induced glycogen synthetase activity due to a blockage of the inhibitory effect of glycogen phosphorylase "a" on glycogen synthetase phosphatase. This enzyme converts glycogen synthetase from the inactive "a" form to the active "b" form. Glycogen breakdown may also be inhibited as a result of phosphorylase "a" inactivation. Glucose production is increased as a result of enhancement of gluconeogenesis. This is due to increased hepatic protein synthesis, transaminase, and phosphoenolpyruvate carboxykinase activity. The catabolic effects of corticosteroids supply more gluconeogenic substrate to the hepatocytes.

The glucagon tolerance test results indicate that it is a sensitive indicator of altered carbohydrate metabolism and hepatic glycogen accumulation. Consequently, the test could be useful in detecting hepatic alteration as a result of hyperglucocorticism whether due to HHA hypersecretion or iatrogenic sources. Seemingly, a complete glucagon tolerance test may not be warranted. A sample for blood glucose determination could be taken before and 30 minutes after glucagon stimulation.

Thus, the glucagon tolerance test can be used as a sensitive indicator of supraphysiologic glucocorticoid levels. It is capable of detecting glucocorticoids use in concentrations as low as those contained in eye drops or ear drops. In general, however, the above data indicates that absolute blood glucose levels of greater than about 300 mg/dl at about 15 or about 30 minutes is evidence of supraphysiologic glucocorticoid influence on hepatic glycogen storage. Normal dogs, for example, characteristically do not have blood glucose values of greater than about 262 mg/dl; and these peak at about 15 minutes. Therefore, all things considered, and in the absence of diseases such as Cushing's, a glucose value above about 300 mg/dl can be taken as positive evidence of glucocorticoid use in the animal. It should also be noted that the concentrations of the glucagon to establish these reference curves and the glucagon used in the glucagon tolerance test itself may be used in wide ranges of concentrations. Moreover, the times over which such reference curves are established and the dose level at which the animal is challenged can be varied over substantial ranges, if desired. Test periods of less than about 2 hours are preferred, and test periods less than about 1 hour are more preferred. Any number of blood samples may be taken over such test periods. It is also within the scope of the teachings of this invention that a single blood sample be used to establish supraphysiological glucocorticoid levels. The determination of the frequency of such test is well within the ability of those skilled in the art. It should be specifically noted, however, that the taking of a blood sample from dogs after about fifteen minutes and before about 35 minutes from the glucagon administration is a highly preferred embodiment of this invention. Those skilled in the art will also appreciate that this test may be carried out by a variety of glucagon tolerance test equipment and procedures, e.g., digitized equipment having LED readouts, wet-chemistry indicators, etc. However, for field use, a simple glucose indicator tape, preferably one designed to show a positive reading above about a 300 mg/dl blood glucose level, would represent is a highly preferred embodiment of the method and an apparatus for carrying out the method of this invention. Perhaps the most convenient apparatus to carry out the method of this invention in the field would be a kit comprised of a glucagon loaded hypodermic syringe, a catheter for collecting samples of the animal's blood, a fluoride containing blood collection tube to inhibit glycolysis and a glucose indicator tape having a positive indicator at a blood glucose level of about 300 mg/dl. Those skilled in the art will appreciate that the methods of this invention may be carried out with apparatus elements other than those suggested for the above field use kit without departing from the scope and spirit of this invention. In short, the applicant's invention is not to be limited by the specific concentrations, test times, glucagon levels, administration or collection equipment specified herein. On the contrary, many changes may be made carrying out the above methods without departing from the spirit and scope of the invention. Therefore, it is intended that all matter contained in the above description shall be interpreted as illustrative and not in a limiting sense. It is also to be understood that the following claims are intended to cover all of the generic and specific features of the invention herein described, and all statements of the scope of the invention, which, as a matter of language, might be said to fall there between. By way of example those skilled in the art will particularly recognize that the methods and apparatus hereinafter claimed may be used to detect ACTH stimulated glucocorticoids as well as directly administered glucocorticoids. Similarly, blood glucose levels may be determined by a variety of instruments other than glucose indicator types.

Thus having disclosed the invention, what is claimed is:

1. A method for detecting supraphysiological levels of glucocorticoids in an animal, comprising the steps of:
   (a) administering a pharmacological dose of glucagon to an animal suspected of having supraphysiological glucocorticoid levels;
   (b) taking a blood sample from the animal between about 15 and about 60 minutes after the glucagon administration; and
   (c) comparing the blood glucose level of the sample with a blood glucose level of 300 mg/dl to indicate glucocorticoid use.

2. A method for detecting supraphysiological levels of glucocorticoids in an animal, comprising the steps of:
   (a) establishing a reference curve of blood glucose levels indicating glucocorticoid use;
   (b) administering a pharmacological dose of glucagon to an animal suspected of having supraphysiological glucocorticoid levels;
   (c) taking one or more blood sample(s) from the animal over a time period used in establishing the reference curve;
   (d) determining the blood glucose level of the sample(s); and
   (e) comparing the blood glucose level of the sample(s) to the reference curve to determine whether there is an excess amount of blood glucose in the sample(s) due to glucocorticoid use.

3. The method of claim 1 wherein the time period used in establishing the reference curve is less than about one hour.

4. The method of claim 1 wherein the blood samples are taken at about 15, 30 and 60 minutes after administering the glucagon.

5. The method of claim 1 wherein the blood sample is taken at about 30 minutes after administering the glucagon.

6. A method for detecting supraphysiological levels of glucocorticoids in a dog, comprising the steps of:
   (a) establishing a reference curve for a normal dog blood glucose response to about 1 0.03 mg/Kg to about a 0.14 mg/Kg to the dog;
   (b) administering a glucagon dose of from about 0.03 mg/Kg to about 0.14 mg/Kg to the dog;
   (c) taking at least one blood sample from the dog between about 15 and about 60 minutes after administration of the glucagon;
   (d) determining the blood glucose level of the sample; and
   (e) comparing the sample's blood glucose level with the reference curve to indicate glucocorticoid use.

7. A method for detecting supraphysiological levels of glucocorticoids in a dog, comprising the steps of:
   (a) establishing a reference curve for a normal dog blood glucose response to about a 0.03 mg/Kg to about a 0.14 mg/Kg dose of glucagon over about a one hour time period;
   (b) administering a glucagon dose of from about 0.03 mg/Kg to about 0.14 mg/Kg to the dog;
   (c) taking a blood sample from the dog at 30 minutes after administration of the glucagon;
   (d) determining the blood glucose level of the sample by use of a color indicator tape sensitive to blood glucose; and
   (e) comparing the sample's blood glucose level with the reference curve to indicate glucocorticoid use.

8. A method for detecting supraphysiological levels of glucocorticoids in a horse, comprising the steps of:
   (a) establishing a reference curve for a normal horse blood glucose response to about a 0.074 mg/Kg does of glucagon over about a one hour time period;
   (b) administering a glucagon dose of about 0.0074 mg/Kg to the horse;
   (c) taking at least one blood sample from the horse between about 15 and about 60 minutes after administration of the glucagon;
   (d) determining the blood glucose level of the sample; and
   (e) comparing the sample's blood glucose level with the reference curve to indicate glucocorticoid use.

9. A method for detecting supraphysiological levels of glucocorticoids in a horse, comprising the steps of:
   (a) establishing a reference curve for the normal horse blood glucose response to about a 0.0074 mg/Kg glucagon over about a one hour time period;
   (b) administering a glucagon dose of about 0.0074 mg/Kg to the horse;
   (c) taking a blood sample from the horse at 30 minutes after administration of the glucagon;
   (d) determining the blood glucose level of the sample by use of color indicator tape sensitive to blood glucose; and
   (e) comparing the sample's blood glucose level with the reference curve to indicate glucocorticoid use.

* * * * *